United States Patent [19]

O'Neil et al.

[11] Patent Number: 5,755,800
[45] Date of Patent: May 26, 1998

[54] MODULAR JOINT PROSTHESIS AUGMENTATION SYSTEM

[75] Inventors: Michael J. O'Neil, West Barnstable; Justin Dye, Mansfield, both of Mass.

[73] Assignee: Johnson & Johnson Professional, Inc., Raynham, Mass.

[21] Appl. No.: 772,727

[22] Filed: Dec. 23, 1996

[51] Int. Cl.$^6$ ........................... A61F 2/38
[52] U.S. Cl. ........................... 623/20
[58] Field of Search ........................... 623/16, 18, 20

[56] References Cited

U.S. PATENT DOCUMENTS

| | | | |
|---|---|---|---|
| 1,664,566 | 4/1928 | Marshall. | |
| 1,816,970 | 8/1931 | Hess. | |
| 2,490,364 | 12/1949 | Livingston | 128/92 |
| 2,616,328 | 11/1952 | Kingsmore | 85/40 |
| 3,076,453 | 2/1963 | Tronzo | 128/92 |
| 4,312,614 | 1/1982 | Palmer et al. | 411/44 |
| 4,353,135 | 10/1982 | Forte et al. | 3/1.911 |
| 4,662,889 | 5/1987 | Zichner et al. | 628/20 |
| 4,711,232 | 12/1987 | Fischer et al. | 128/92 |
| 4,731,086 | 3/1988 | Whiteside et al. | 623/20 |
| 4,769,039 | 9/1988 | Horber | 623/20 |
| 4,778,473 | 10/1988 | Matthews et al. | 623/20 |
| 4,822,366 | 4/1989 | Bolesky | 623/20 |
| 4,878,791 | 11/1989 | Kurihara et al. | 411/55 |
| 4,936,847 | 6/1990 | Manginelli | 623/23 |
| 4,936,853 | 6/1990 | Fabian et al. | 623/20 |
| 4,950,298 | 8/1990 | Gustilo et al. | 623/20 |
| 4,952,106 | 8/1990 | Kubogochi et al. | 411/48 |
| 4,971,500 | 11/1990 | Benoit et al. | 411/182 |
| 5,019,103 | 5/1991 | Van Zile et al. | 623/20 |
| 5,039,267 | 8/1991 | Wollar | 411/508 |
| 5,062,852 | 11/1991 | Dorr et al. | 623/20 |
| 5,108,446 | 4/1992 | Wagner et al. | 623/22 |
| 5,152,796 | 10/1992 | Slamin | 623/20 |
| 5,201,769 | 4/1993 | Schutzer | 623/23 |
| 5,222,984 | 6/1993 | Forte | 623/22 |
| 5,226,915 | 7/1993 | Bertin | 623/20 |
| 5,268,001 | 12/1993 | Nicholson et al. | 606/72 |
| 5,344,461 | 9/1994 | Philpot | 623/20 |
| 5,370,693 | 12/1994 | Kelman et al. | 623/16 |
| 5,387,241 | 2/1995 | Hayes | 623/20 |
| 5,429,467 | 7/1995 | Gugle et al. | 411/182 |
| 5,531,793 | 7/1996 | Kelman et al. | 623/16 |
| 5,549,685 | 8/1996 | Hayes | 623/20 |
| 5,549,687 | 8/1996 | Coates et al. | 623/20 |
| 5,556,433 | 9/1996 | Gabriel et al. | 623/18 |
| 5,571,194 | 11/1996 | Gabriel | 623/20 |
| 5,609,642 | 3/1997 | Johnson et al. | 623/20 |
| 5,609,645 | 3/1997 | Vinciguerra | 623/20 |

FOREIGN PATENT DOCUMENTS

| | | | |
|---|---|---|---|
| 2702651 | 9/1994 | France | 623/20 |
| 2223174 | 4/1990 | United Kingdom. | |

*Primary Examiner*—Michael J. Milano
*Assistant Examiner*—Tram Anh T. Nguyen
*Attorney, Agent, or Firm*—Nutter, McClennen & Fish, LLP

[57] ABSTRACT

A modular joint prosthesis system includes an articulation member, such as a cruciate retaining femoral component of a knee joint prosthesis, having a superior bone engaging surface, an inferior articulation surface and one or more fixation pegs extending from the superior surface. An augmentation block mounts on the superior surface of the articulation member and has an aperture surrounding a respective fixation peg. The system further includes a compression collet seated between the aperture of the augmentation block and the fixation peg. In assembly, a securement device mounted over the fixation peg compresses the compression collet so as to engage the fixation peg and maintain the augmentation block on the articulation member.

26 Claims, 4 Drawing Sheets

MODULAR JOINT PROSTHESIS AUGMENTATION SYSTEM

CROSS REFERENCE TO RELATED APPLICATION

Not Applicable.

STATEMENTS REGARDING FEDERALLY SPONSORED RESEARCH

Not Applicable.

BACKGROUND OF THE INVENTION

The invention relates to an enhanced joint prosthesis augmentation system for use with conventional prosthesis components, having a minimal number of unique parts, and providing different geometries of bone engaging surfaces to enhance securement of the prosthesis.

Joint arthroplasty is a well known surgical procedure by which a diseased and/or damaged natural joint, such as a knee, hip or elbow joint, is replaced with a prosthetic joint. The health and condition of the joint to be replaced dictate the type of prosthesis that can suitably be used to replace the natural joint. For example, knee prostheses, and particularly femoral components of knee prostheses, are available in different designs to meet the needs of different patient conditions.

One type of femoral component for knee joint prostheses is known as a cruciate retaining femoral component since it is useful where a patient's cruciate ligaments are not sacrificed during the knee arthroplasty procedure. This type of femoral component typically has fixation pegs integrally mated upon the medial and lateral distal flats of the superior surface of the prosthesis to stabilize the prosthesis upon mounting to the femur. The cruciate ligaments also contribute to the stability of the artificial knee joint.

Another type of femoral component for a knee joint prosthesis, known as a cruciate sacrificing femoral component, is useful where the patient's cruciate ligaments are nonfunctional or must be removed in the course of the knee arthroplasty procedure. Cruciate sacrificing femoral components typically have an intercondylar notch in the form of a box formed on a superior, bone engaging surface.

In some instances, due to disease or trauma, insufficient healthy bony mass exists at the distal end of a bone (e.g., the femur) to which a joint prosthesis is to be secured. In these instances, it may become necessary to remove additional portions of bone in an asymmetrical manner, to ensure sufficient anchoring and proper fit of the prosthesis. As a result, it is sometimes necessary to augment the superior portion of the femoral component of the prosthesis in order to add additional thickness to the prosthesis to compensate for the asymmetrical contour of the bone.

The superior surface of a femoral component can be augmented by adding one or more augmentation blocks of appropriate height and shape to the component. Various types of augmentation blocks are known to those having ordinary skill in the art.

One type of augmentation block is secured to the prosthesis by cement. However, this technique for augmentation block attachment disadvantageously results in a process delay to permit curing of the cement and, further, does not provide the surgeon with flexibility during the arthroplasty procedure to try different augmentation block geometries to optimize the fit of the prosthesis.

Another type of augmentation system is disclosed in U.S. Pat. No. 4,936,847 (Manginelli) in which the augmentation device is secured to the prosthesis by a mechanical interlocking arrangement, rather than by cement. The Manginelli system, although useful, requires a specially constructed femoral component to secure the augmentation block. Such a custom femoral component may be costly to manufacture and supply, particularly since in some instances, augmentation is not required.

SUMMARY OF THE INVENTION

The present invention relates to an improved modular joint prosthesis augmentation system particularly well suited for use with prosthesis components having one or more stabilizing fixation pegs, such as a femoral component of a knee joint prosthesis. It will thus be appreciated that the inventive concepts described herein are applicable to a variety of joint prostheses in which augmentation is sometimes necessary.

The invention comprises a modular joint prosthesis system including an articulation member having a superior bone engaging surface and an inferior articulation surface, with the superior surface having at least one fixation peg extending therefrom. An augmentation block, having an aperture dimensioned to surround a respective fixation peg, is mounted on the superior surface of the articulation member with the use of a compression collet and a securement device. The compression collet is seated between the aperture of the augmentation block and the respective fixation peg and the securement device is mountable over the fixation peg. In assembly, the securement device compresses the compression collet against the fixation peg so as to maintain the augmentation block in engagement with the articulation member. In the illustrative knee joint application, the articulation member is a cruciate retaining femoral component and the fixation pegs extend from the medial and lateral distal flats.

The augmentation system is adapted for use with conventional prosthesis components having fixation pegs, without requiring any custom features to be provided. This arrangement is advantageous since such custom features can be costly to manufacture and, in fact, are unnecessary in situations where augmentation is not required.

In the illustrative knee joint application, in which the articulation member is a femoral component, a universal augmentation block has an elongated aperture and is sized and shaped to augment either the medial or lateral distal flat of the femoral component. In this way, the number of unique parts associated with the augmentation system is minimized.

In accordance with one embodiment, the collet includes a base portion sized and shaped to be seated within the aperture of the augmentation block, a plurality of compressible members extending from the base portion to define a substantially circular opening and an intermediate, externally threaded portion between the base portion and the compressible members. The inner diameter of the opening defined by the compressible members is slightly greater than, less than or equal to the diameter of the fixation peg member and may taper from the proximal portion adjacent to the threaded portion toward the distal portion thereof. The securement device is a nut having internal threads matable with the external threads of the collet.

In use, engagement of the internal threads of the securement nut with the external threads of the collet and advancement of the nut over the collet cause interior surfaces of the nut to compress the compressible collet members against the fixation peg member.

The compression forces thus applied are sufficient to maintain the augmentation block in secure engagement with the articulation member.

In one embodiment, the augmentation block aperture is elongated in the medial-lateral direction, and the base portion of the collet is similarly shaped and dimensioned such that it is able to be disposed within the aperture. The elongated aperture, together with the shape and dimensions of the augmentation block and the collet, advantageously render the block suitable for mounting on either the medial or lateral distal flat of a left or right side prosthesis, thereby minimizing the number of unique parts associated with the augmentation system.

In accordance with an alternate embodiment, the aperture of the augmentation block is substantially circular and includes internal threads. The collet is likewise substantially circular and has an annular collar and a plurality of compressible members extending from the collar, with the outermost diameter of the collar being slightly greater than or equal to the diameter of the augmentation block aperture. The securement device is an annular nut having external threads matable with the internal threads of the augmentation block aperture.

In use, the external threads of the securement device are mated with the internal threads of the augmentation block aperture. Advancement of the securement device over the fixation peg member causes interior surfaces of the nut to compress the compressible collet members against the fixation peg member with sufficient force to maintain the augmentation block in secure engagement with the articulation member.

Different geometries of the bone engaging portions of the prosthesis are described in order to permit optimization of the prosthesis securement. In particular, in one embodiment, the securement nut has a head which covers the end of the fixation peg member in assembly and contacts bone. In another embodiment, the securement nut is advanced over the fixation peg to terminate at an intermediate location of the fixation peg. With this arrangement, the end of the fixation peg is exposed to engage bone.

DETAILED DESCRIPTION OF THE INVENTION

Referring to FIGS. 1–4, a modular joint prosthesis augmentation system 10 in accordance with the invention includes an articulation member 14 requiring augmentation for optimum mounting to a patient's bone. In the illustrative embodiment, the articulation member 14 is a cruciate retaining femoral component of a knee joint prosthesis, which is assumed to be a left side prosthesis. It is understood however, that the inventive augmentation system described herein is suitable for use with a variety of joint prostheses.

Figure 1:
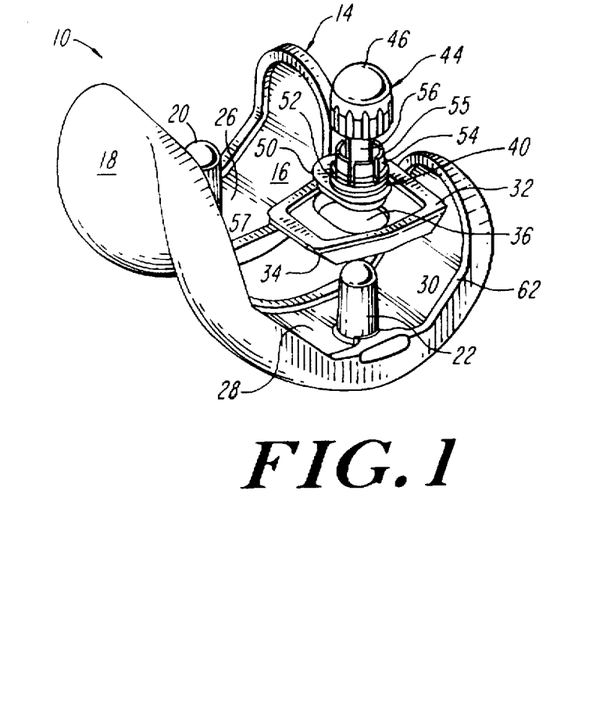
FIG. 1 is an exploded isometric view of a cruciate retaining femoral component of a knee joint prosthesis having a modular augmentation system according to the invention.
Figure 2:
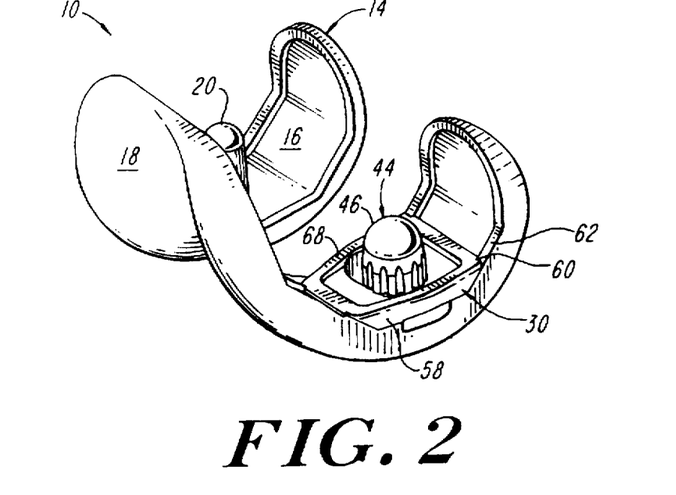
FIG. 2 is an isometric view of the augmented cruciate retaining femoral component of FIG. 1 in assembly.
Figure 3:
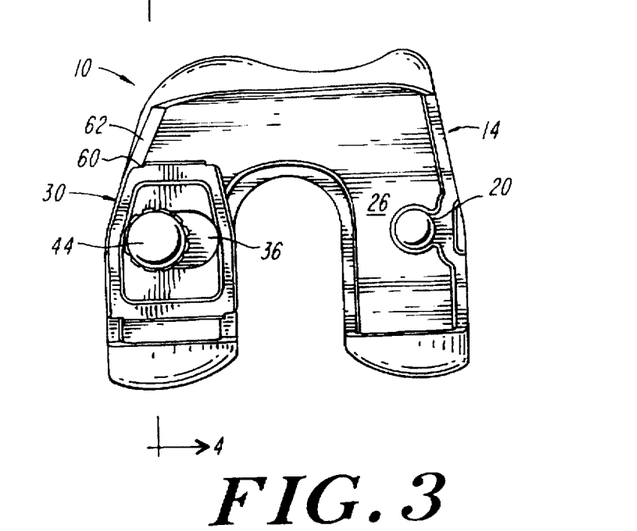
FIG. 3 is a top plan view of the augmented cruciate retaining femoral component of FIG. 2.
Figure 4:
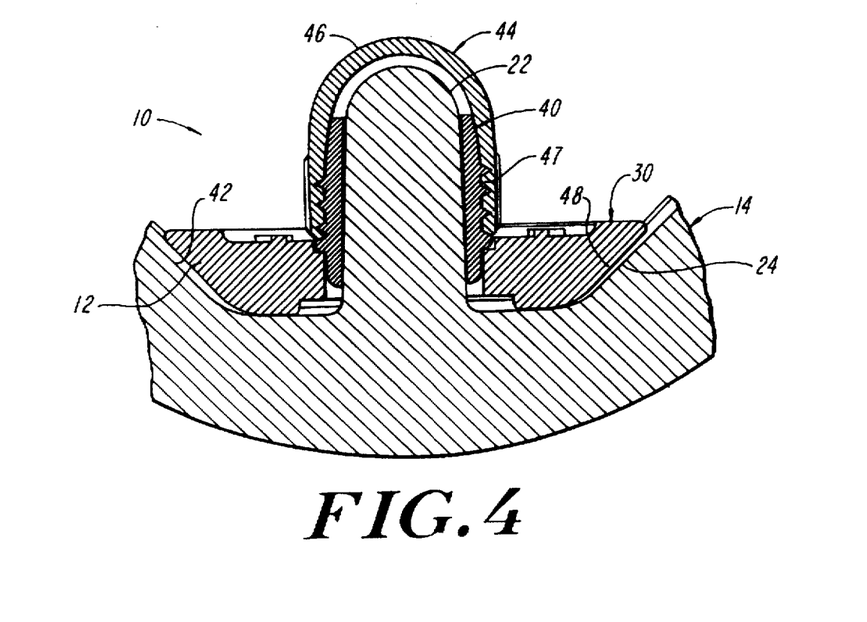
FIG. 4 is a sectional view of the augmented cruciate retaining femoral component of FIG. 3.

As shown in the exploded view of FIG. 1, the articulation member 14 has a superior bone engaging surface 16 and an inferior articulation surface 18. At least one, and in the illustrative embodiment two, elongate fixation peg members 20, 22 extend superiorly from the superior surface 16 of the articulation member.

The illustrative cruciate retaining femoral component 14 further includes two opposed, canted surfaces 12, 24 (FIG. 4), referred to, respectively, as the anterior and posterior chamfers. The anterior and posterior chamfers 12, 24 are spaced by the medial distal flat 26 and the lateral distal flat 28. The fixation peg members 20, 22 extend superiorly from the medial distal flat 26 and the lateral distal flat 28, respectively.

An augmentation block 30 mounts on the superior surface 16 of the articulation member 14. More particularly, one or more augmentation blocks of the same or different heights may be disposed upon one or both of the medial and lateral distal flats 26, 28, depending on the particular contour of the patient's femur. For illustrative purposes, a single augmentation block 30 is provided for mounting upon the lateral distal flat 28.

The augmentation block 30 has a superior bone engaging surface 32 and an inferior surface 34 disposed adjacent to the superior surface 16 of the articulation member 14 in assembly. Preferably, the augmentation block 30 is shaped and dimensioned to complement the superior contour of the articulation member 14 in order to facilitate proper seating of the block 30 within the articulation member 14. To this end, the augmentation block 30 has two, opposed inferior canted surfaces 42, 48 (FIG. 4) which are angled to complement the articulation member anterior and posterior chamfers 12, 24, respectively. The augmentation block canted surfaces 42, 48 can be either posterior or anterior surfaces, depending on whether the augmentation block is mounted on the medial or lateral side, or on a left or right side prosthesis.

Augmentation block 30 further includes side surfaces 58, 68 (FIG. 2) which correspond to either medial or lateral facing surfaces, depending on whether the augmentation block 30 is used on the lateral or medial side of a prosthesis, or in a left or right side prosthesis. Side surfaces 58, 68 are substantially vertical and extend at a right angle to the plane of the superior and inferior surfaces 32, 34.

An aperture 36 extends through the augmentation block 30 and is sized and shaped to at least surround a respective fixation peg member 22. In the embodiment of FIGS. 1–4, the augmentation block aperture 36 is elongated in the medial-lateral direction, as shown. Together with the shape and dimensions of the augmentation block 30, the elongate aperture 36 permits the augmentation block to be mounted over either the medial distal flat 26 or the lateral distal flat 28. Reference to the plan view of FIG. 3 reveals that the augmentation block 30 may alternatively be located over the medial distal flat 26, in which case the exposed portion of the aperture would be opposite that portion exposed when the block 30 is mounted over the lateral distal flat 28 as shown. With this arrangement, the augmentation block 30 can be considered to be a "universal" augmentation block, which advantageously minimizes the number of unique parts associated with the prosthesis.

A compression collet 40 is provided with a base portion 50 which, like the augmentation block aperture 36, is elongated in the medial-lateral direction. The collet 40 further has an intermediate portion 52, which in a preferred embodiment is externally threaded, and a plurality of compressible members 54 extending proximally from the intermediate portion. The compressible members 54 are arranged so as to define a substantially circular opening 56 having an inner diameter slightly greater than, less than or equal to the diameter of the fixation peg member 22. In particular, the inner diameter of the opening 56 may be less than or greater than the diameter of the fixation peg member 22 by approximately 0.001 to 0.100 inches. The compressible members 54 each include a proximal end 55 and a distal end 57 that is adjacent intermediate portion 52. The inner diameter of the opening 56 may be tapered so as to narrow from the distal end adjacent to the threaded portion 52 to the proximal end thereof.

A securement device 44 is provided for mounting over the fixation peg member 22 to compress the compressible members 54 of the collet into engagement with the fixation peg member so as to maintain the augmentation block 30 on the articulation member 14. Thus, the securement device 44 controls the compression of the compressible members 54. In the embodiment of FIGS. 1–4, the securement device 44 is a nut having internal threads 47 adapted for mating with the external threads 52 of the collet 40, as shown in the sectional view of FIG. 4.

The securement device 44 may take the form of a nut having a head 46 which covers the fixation peg member 22 in assembly, so as to provide a continuous fixation peg member for contacting the femur. It will be appreciated however, that the external geometry and features of the securement device 44 can be readily modified to enhance fixation of the prosthesis to the bone. Alternatively, the augmentation system of the present invention permits the fixation peg member itself to engage bone, as in the embodiment of FIGS. 5–7 described below.

It is understood that the securement device 44 may be of a construction other than that illustrated in FIGS. 1–4. For example, the securement device 44 need not have a head 46 that covers the fixation peg. Moreover, neither the securement device 44 nor the collet need have interlocking threads. One of ordinary skill in the art will appreciate that other interlocking structures may be used on both the securement device and the collet to compress compressible members 54 and to enable the securement device to securely engage the collet.

In assembly, the compression collet 40 is seated between the augmentation block aperture 36 and the fixation peg member 22 and the securement device 44 is mounted over the fixation peg member 22. Once the securement device 44 is mated to the collet 40, advancement of the securement device 44 causes compression of the compressible members 54 against the fixation peg member 22, thereby resulting in the augmentation block 30 being retained in engagement with the fixation peg member 22.

More particularly, the prosthesis augmentation system 10 is assembled by placing the augmentation block 30 over the superior surface 16 of the articulation member 14, with the inferior canted surfaces 42, 48 of the augmentation block abutting the anterior and posterior chamfers 12, 24 on the superior surface of the femoral articulation member 14, respectively, and the augmentation block aperture 36 surrounding the fixation peg member 22. Orientation keys in the form of corner notches 60 of the augmentation block 30 mate with grooves 62 along the edges of the flat 28 in order to prevent lateral movement of the block 30 relative to the femoral component 14.

The collet 40 is then seated over the augmentation block 30, with the elongate base portion 50 aligned with the elongate aperture 36. Preferably, the size and shape of the base portion 50 is complementary with respect to the augmentation block aperture 36 so that the collet 40 is engaged within the aperture 36 by a friction fit. When the collet 40 is in a non-compressed condition, there is little or no frictional and/or mechanical engagement between the collet 40 and the fixation peg member 22.

With the base 50 of the collet 40 thus frictionally engaged within the augmentation block aperture 36, the securement device 44 is engaged with the collet and is advanced with a sufficient torque to compress the compressible members 54 of the collet toward the fixation peg member 22. When the collet 40 is in the compressed condition (FIG. 4), sufficient frictional and/or mechanical engagement exists between the compressible collet members 54 and the fixation peg member 22 to cause the augmentation block 30 to be securely and reliably maintained in position with respect to the femoral articulation member 14. In the illustrative embodiment 10, a suitable tensile attachment force (e.g., about 10 to 500 kg) can be achieved by applying a torque in the range of about 20–40 in-lbs to the securement nut 44.

Securement forces of the augmentation system can be varied by, for example, varying the torque applied to the securement device 44, the internal taper of the securement device, the external taper of the collet 40, the internal geometry and finish of the collet and/or the finish and/or geometry of the fixation peg member. For example, undercuts on the fixation peg member can be incorporated to further enhance securement of the augmentation system.

As is now apparent, the present augmentation system is utilized with a conventional prosthesis articulation member 14 having fixation pegs. Thus, the augmented prosthesis component advantageously does not require custom features for accommodating the augmentation system.

Figure 5:
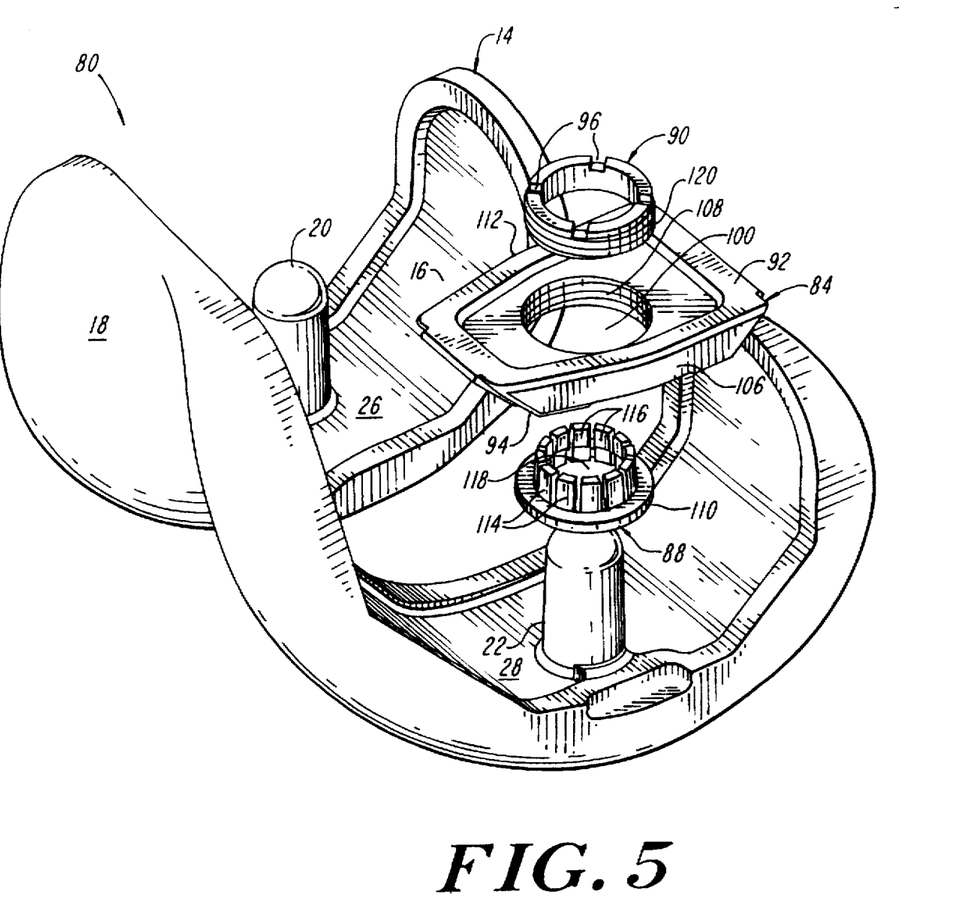
FIG. 5 is an exploded isometric view of a cruciate retaining femoral component of a knee joint prosthesis having a modular augmentation system according to a further embodiment of the invention.
Figure 6:
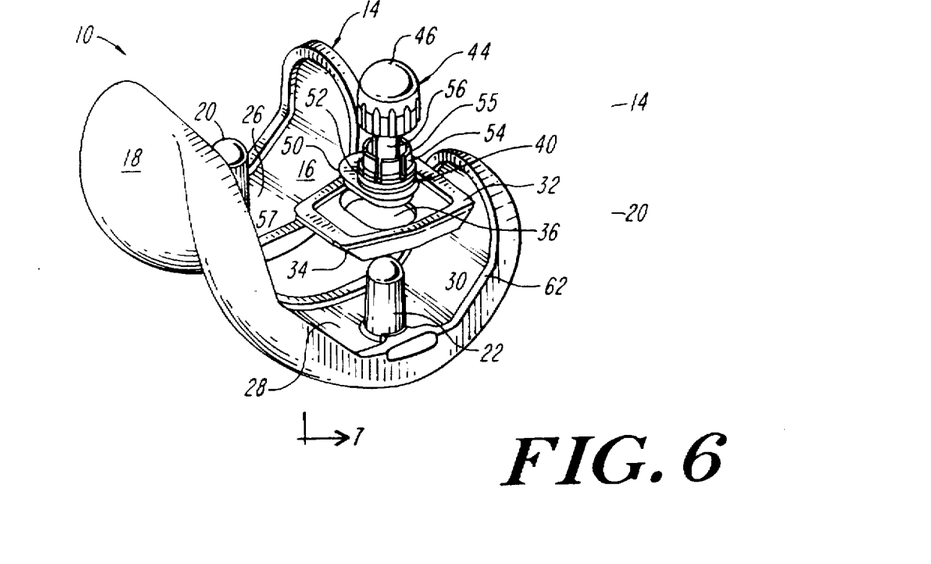
FIG. 6 is a top plan view of the augmented cruciate retaining femoral component of FIG. 5 in assembly.
Figure 7:
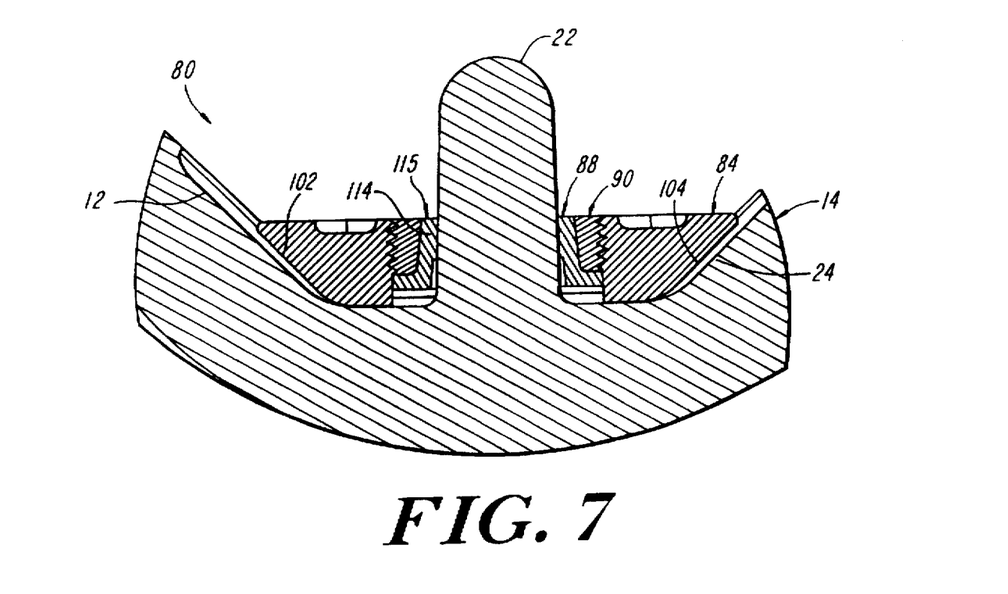
FIG. 7 is a sectional view of the augmented cruciate retaining femoral component of FIG. 6.

Referring also to FIGS. 5–7, an alternate embodiment 80 of the inventive modular joint prosthesis augmentation system is shown to include a left side articulation member 14 having features as described above in conjunction with FIGS. 1–4, including fixation peg members 20, 22 extending superiorly from the medial and lateral distal flats 26, 28. The system 80 further includes an augmentation block 84, a compression collet 88 and a securement device 90.

The augmentation block 84 has a superior bone engaging surface 92 and an inferior surface 94 disposed opposite the superior surface 16 of the articulation member 14 in assembly. More particularly, the augmentation block 84 has two, opposed inferior canted surfaces 102, 104 which are complementarily angled with respect to the articulation member anterior and posterior chamfers 12, 24, respectively. Augmentation block 84 further includes side surfaces 106, 112 which correspond to either medial or lateral facing surfaces, depending on whether the augmentation block 84 is used on the lateral or medial side of a prosthesis, or in a left or right side prosthesis. Side surfaces 106, 112 are substantially vertical and extend at a right angle to the plane of the superior and inferior surfaces 92, 94.

An aperture 100 extends through the augmentation block 84 from its superior surface 92 to its inferior surface 94. Aperture 100 is substantially circular in shape and preferably includes internal threads 108 for mating with the securement device 90, as will be described.

The compression collet 88 is substantially circular in shape and has an annular collar 110 and a plurality of compressible members 114 extending proximally from the collar. The compressible members 114 define a substantially circular opening 118 having a diameter slightly greater than, less than or equal to the diameter of the fixation peg member 22. The diameter of the opening 118 may taper from the distal end adjacent to the collar 110 toward the proximal end. The outermost diameter of the collar 110 is slightly greater than or equal to the diameter of the augmentation block aperture 100. Preferably, the inner surface of the compressible members 114 includes surface features 116 (FIG. 5), such as protrusions, to enhance engagement with the fixation peg member 22. Similarly, complementary surface features, such as undercuts, may be formed on the fixation pegs to enhance fixation.

The securement device 90 is, in one embodiment, in the form of a nut having external threads 120 matable with the internal threads 108 of the augmentation block aperture 100 and an inner diameter with dimensions suitable to compress the compressible members 114 of the collet 88 against the fixation peg member 22 in assembly. In the illustrative embodiment 80, the interior surface of the nut 90 is tapered so that the inner diameter of the nut is slightly greater at its distal end adjacent to the collet collar 110 than at its proximal end, as shown in FIG. 7. Such a taper serves to enhance the securement forces provided by the securement device 90.

It is understood that securement device 90 may be of a construction other than that illustrated in FIGS. 5-7. Further, neither the securement device 90 nor the inner wall of aperture 100 need include threads. One of ordinary skill in the art will appreciate that other interlocking structures may be used on both the securement device and the augmentation block and/or the collet to compress compressible members 114 against the fixation peg.

Assembly of the augmentation system 80 is achieved by placing the collect 88 over the desired fix the desired fixation peg member 22, so that the inferior surface of the collect collar 110 is disposed in contact with the superior surface 16 of the articulation member 14. Again, in the non-compressed condition, little or no frictional and/or mechanical engagement exists between the compressible members 114 of the collet and the fixation peg member 22.

The augmentation block 84 is then placed over the collet 88, with canted augmentation block surfaces 102, 104 abutting the anterior and posterior chamfers 12, 24, respectively, of the articulation member. In this position, the compressible members 114 extend into the augmentation block aperture 100. Preferably, the proximal end 115 of the compressible members 114 terminates adjacent to the superior surface 92 of the augmentation block, as shown in FIG. 7.

With the collet 88 and augmentation block 84 thus positioned, the securement device 90 is brought into engagement with the augmentation block 84. In the illustrated embodiment, this is accomplished by threading the external threads 120 of the securement device 90 onto the internal threads 108 of the augmentation block 84. The securement device 90 is advanced onto the augmentation block 84 until an inferior surface of the securement device 90 contacts the superior surface of the collet collar 110, as shown in FIG. 7. A tool (not shown) suitable for engaging notches 96 of the securement device 90 can be used to advance the securement device into engagement with the augmentation block aperture 100.

With the securement device 90 thus engaged, the inner surface of the securement device compresses the compressible collet members 114 against the fixation peg member 22.

In particular, this compression force is sufficient to maintain the augmentation block 84 in secure engagement with the femoral articulation component 14. In the illustrative embodiment of FIGS. 5-7, a suitable tensile attachment force (e.g., about 10 to 500 kg) can be achieved by applying a torque in the range of about 20-40 in-lbs to the securement device 90.

As shown in FIGS. 6 and 7, in assembly, the top of the fixation peg member 22 is exposed and thus provides a bone engaging surface of the prosthesis, as may be desirable. Like the embodiment of FIGS. 1-4, the augmentation system 80 is advantageously utilized with a conventional articulation member 14, without requiring costly custom features to be provided.

The dimensions of the various components of the augmentation system embodiments described herein can vary depending on the particular requirements of a given application. One of ordinary skill in the art can readily determine the appropriate dimensions and relative dimensions of the components.

The prostheses components of the invention, including the articulation member and augmentation blocks, can be made from a variety of biocompatible materials having high strength, durability and resistance to wear debris. Examples of such materials include metal alloys such as cobalt chromium alloys, titanium alloys, stainless steel, ceramics and other materials, including polymers, that are well known for use in the manufacture of implantable bone prostheses. A preferred material for these prostheses components is a cobalt chromium alloy such as ASTM F-75.

The collet preferably is made from a malleable metal or metal alloy to reduce the risk of tensile failure as a result of compression. Where such materials are used to form a threaded component, the materials should be able to deform (but not fail) when subjected to a torque of about 20 to 65 in-lbs, and more preferably about 25-35 in-lbs. A preferred material is a wrought cobalt chromium alloy such as ASTM F-90.

The securement devices are preferably made from a metal or metal alloy that has a higher modulus and a greater hardness than does the collet. Such properties ensure that the collet will deform when subjected to torque and/or axial load. A preferred material is wrought cobalt chromium alloy such as ASTM F-1537. (formerly known as ASTM F799).

The foregoing description of the illustrative embodiments of the invention is presented to indicate the range of constructions to which the invention applies. Variations in the physical architecture and dimensions of the invention will be apparent to those having ordinary skill in the art based upon the disclosure herein, and such variations are considered to be within the scope of the invention in which patent rights are asserted, as set forth in the claims appended hereto. All publications and references cited herein are expressly incorporated herein by reference in their entirety.

What is claimed is:

1. A modular joint prosthesis system, comprising:
   at least one articulation member having a superior bone engaging surface and an inferior articulation surface, the superior surface including at least one fixation peg member extending superiorly therefrom;
   at least one augmentation block having a superior bone engaging surface, an inferior surface that mounts upon the superior surface of the articulation member and an aperture extending between the superior and inferior surfaces, the aperture having dimensions suitable to surround the at least one fixation peg member;

at least one compression collet having a size and shape effective to be seated between the aperture of the augmentation block and the at least one fixation peg member, wherein the at least one compression collet is engaged within the aperture; and at least one securement device mountable to the at least one fixation peg member to compress the at least one compression collet so as to engage the at least one fixation peg member and maintain the augmentation block upon the articulation member.

2. The system of claim 1 wherein the at least one articulation member is a femoral component of a knee joint prosthesis.

3. The system of claim 2 wherein the femoral component is a cruciate retaining femoral component with a first fixation peg member extending from a medial distal flat of the femoral component and a second fixation peg member extending from a lateral distal flat of the femoral component.

4. The system of claim 3 wherein the at least one compression collet comprises:

a base portion which seats within the aperture of the at least one augmentation block; and a plurality of compressible members extending from the base portion.

5. The system of claim 4 wherein the at least one compression collet further comprises an intermediate, externally threaded portion disposed between the base portion and the compressible members.

6. The system of claim 5 wherein the compressible members define a substantially circular opening having an inner diameter slightly greater than, less than or equal to the diameter of the at least one fixation peg member.

7. The system of claim 6 wherein the inner diameter of the opening defined by the compressible members tapers from a distal portion thereof adjacent to the intermediate portion to a proximal portion thereof.

8. The system of claim 6 wherein the at least one securement device comprises a nut having internal threads matable with the external threads of the at least one compression collet.

9. The system of claim 3 wherein the aperture of the at least one augmentation block is elongated in the medial-lateral direction.

10. The system of claim 9 wherein the at least one compression collet comprises:

a base portion, elongated in the medial-lateral direction, which seats within the aperture of the at least one augmentation block;

an intermediate, externally threaded portion; and a plurality of compressible members extending from the intermediate portion.

11. The system of claim 10 wherein the intermediate portion of the at least one compression collet is disposed on the base portion offset from a center point of the base portion.

12. The system of claim 4 wherein the base portion of the at least one compression collet is frictionally engaged with the aperture of the at least one augmentation block.

13. The system of claim 3 wherein the aperture of the at least one augmentation block is substantially circular.

14. The system of claim 13 wherein the aperture of the at least one augmentation block is defined by a threaded inner wall.

15. The system of claim 14 wherein the at least one compression collet is substantially circular having an annular collar and a plurality of compressible members extending from the collar.

16. The system of claim 15 wherein the collar has an outermost diameter slightly greater than or equal to a diameter of the aperture of the at least one augmentation block.

17. The system of claim 16 wherein the at least one securement device comprises an annular nut having external threads matable with the threaded inner wall of the aperture of the at least one augmentation block, and an inner diameter with dimensions suitable to compress the compressible members of the at least one compression collet against the at least one fixation peg member upon mating with the at least one augmentation block.

18. The system of claim 16 wherein internal surfaces of the compressible members include surface features to enhance engagement with the at least one fixation peg member.

19. A modular joint prosthesis system, comprising:

at least one articulation member having a superior bone engaging surface and an inferior articulation surface, the superior surface including at least one fixation peg member extending superiorly therefrom;

at least one augmentation block having a superior bone engaging surface, an inferior surface that mounts upon the superior surface of the at least one articulation member and an aperture extending between the superior and inferior surfaces, the aperture having dimensions suitable to surround the at least one fixation peg member;

at least one compression collet comprising:

a base portion which seats within the aperture of the at least one augmentation block; an intermediate portion; and a plurality of compressible members extending from the intermediate portion; and at least one securement device matable with the intermediate portion of the at least one compression collet to compress the at least one compression collet so as to engage the at least one fixation peg member and maintain the at least one augmentation block upon the at least one articulation member.

20. The system of claim 19 wherein the intermediate portion of the at least one compression collet has external threads and the at least one securement device has internal threads matable with the external threads of the intermediate portion.

21. The system of claim 19 wherein the aperture of the at least one augmentation block is elongated in the medial-lateral direction and the base portion of the at least one compression collet is elongated in the medial-lateral direction.

22. The system of claim 19 wherein the compressible members define an opening which tapers from a distal portion thereof adjacent to the intermediate portion of the at least one compression collet to a proximal portion thereof.

23. The system of claim 19 wherein the base portion of the at least one compression collet is frictionally engaged with the aperture of the at least one augmentation block.

24. A modular joint prosthesis system, comprising:

at least one articulation member having a superior bone engaging surface and an inferior articulation surface, the superior surface including at least one fixation peg member extending superiorly therefrom;

at least one augmentation block having a superior bone engaging surface, an inferior surface that mounts upon the superior surface of the at least one articulation member and an aperture extending between the superior and inferior surfaces, the aperture having dimensions suitable to surround the at least one fixation peg member;

at least one compression collet having an annular collar and a plurality of compressible members extending from the collar; and at least one securement device matable with the aperture of the at least one augmentation block to compress the at least one compression collet so as to engage the at least one fixation peg member and maintain the at least one augmentation block upon the at least one articulation member.

25. The system of claim 24 wherein the aperture of the at least one augmentation block is substantially circular and is defined by a threaded inner wall and the at least one securement device has external threads matable with the threaded inner wall of the aperture of the at least one augmentation block.

26. The system of claim 24 wherein internal surfaces of the compressible members include surface features to enhance engagement with the at least one fixation peg member.

* * * * *